US012596119B2

(12) United States Patent
Nath et al.

(10) Patent No.: US 12,596,119 B2

(45) Date of Patent: Apr. 7, 2026

(54) ANALYTE DETECTION IMMUNOASSAY

(71) Applicant: Promega Corporation, Madison, WI (US)

(72) Inventors: Nidhi Nath, Madison, WI (US); Rod Flemming, Madison, WI (US); Marjeta Urh, Madison, WI (US)

(73) Assignee: Promega Corporation, Madison, WI (US)

( * ) Notice: Subject to any disclaimer, the term of this patent is extended or adjusted under 35 U.S.C. 154(b) by 779 days.

(21) Appl. No.: 17/729,829

(22) Filed: Apr. 26, 2022

(65) Prior Publication Data

US 2022/0252585 A1 Aug. 11, 2022

Related U.S. Application Data

(62) Division of application No. 15/892,557, filed on Feb. 9, 2018, now Pat. No. 11,327,072.

(60) Provisional application No. 62/456,906, filed on Feb. 9, 2017.

(51) Int. Cl.

*G01N 33/543* (2006.01)
*C07K 16/28* (2006.01)
*G01N 33/58* (2006.01)
*G01N 33/94* (2006.01)

(52) U.S. Cl.

CPC ... *G01N 33/54306* (2013.01); *C07K 16/2863* (2013.01); *G01N 33/58* (2013.01); *G01N 33/582* (2013.01); *G01N 33/94* (2013.01); *C07K 2317/24* (2013.01)

(58) Field of Classification Search

CPC ............ C07K 16/2863; C07K 2317/24; G01N 33/534; G01N 33/54306; G01N 33/58; G01N 33/582; G01N 33/6857; G01N 33/94

See application file for complete search history.

(56) References Cited

U.S. PATENT DOCUMENTS

| | | | |
|---|---|---|---|
| 4,946,778 | A | 8/1990 | Ladner et al. |
| 5,104,793 | A | 4/1992 | Buck |
| 5,260,203 | A | 11/1993 | Ladner et al. |
| 7,238,842 | B2 | 7/2007 | Wood et al. |
| 7,425,436 | B2 | 9/2008 | Darzins et al. |
| 7,858,321 | B2 | 12/2010 | Glezer et al. |
| 8,822,231 | B2 | 9/2014 | Melin et al. |
| 8,859,220 | B2 | 10/2014 | Hawkins et al. |
| 2004/0142392 | A1 | 7/2004 | Templin et al. |
| 2005/0069958 | A1 | 3/2005 | Mills et al. |
| 2016/0054317 | A1 | 2/2016 | Dowell et al. |
| 2016/0161474 | A1 | 6/2016 | Husar et al. |
| 2016/0376568 | A1 | 12/2016 | Duellman et al. |

FOREIGN PATENT DOCUMENTS

| | | |
|---|---|---|
| WO | WO 1988/001649 | 3/1988 |
| WO | WO 2007/098148 | 8/2007 |
| WO | WO 2016/097116 | 6/2016 |
| WO | WO 2016/210294 | 12/2016 |

OTHER PUBLICATIONS

Boute et al., NanoLuc Luciferase—A Multifunctional Tool for High Throughput Antibody Screening. Front Pharmacol. Feb. 18, 2016;7:27.
"Cetuximab", Wikipedia. Apr. 20, 2020. Retrieved from: en.wikipedia.org/wiki/Cetuximab, 7 pages.
Chothia et al., Canonical structures for the hypervariable regions of immunoglobulins. J Mol Biol. Aug. 20, 1987;196(4):901-17.
Chothia et al., Conformations of immunoglobulin hypervariable regions. Nature. Dec. 21-28, 1989;342(6252):877-83.
Hartmann et al., Expanding assay dynamics: a combined competitive and direct assay system for the quantification of proteins in multiplexed immunoassays. Clin Chem. Jun. 2008;54(6):956-63.
Henderson et al., Irreversible inhibitors of methotrexate transport in L1210 cells. Characteristics of inhibition by an N-hydroxysuccinimide ester of methotrexate. Biochim Biophys Acta. Oct. 26, 1983;735(1):123-30.
"Immunoglobulin F(ab) and F(ab')2 fragments. Use of immunoglobulin fragments eliminates non-specific binding between the Fc portions of antibodies and the Fc receptor on cells." Abcam. Apr. 20, 2020. Retrieved from: abcam.com/secondary-antibodies/advantages-of-immunoglobulin-fab-and-fab2-fragments. 4 pages.
Kabat et al., Sequences of Proteins of Immunological Interest (National Institutes of Health, Publication No. 91-3242, vols. 1-3, Bethesda, Md, TOC Only.
International Search Report and Written Opinion for PCT/US2018/017540, mailed Jun. 25, 2018, 13 pages.
Extended EP Search Report for EP18751757, mailed Oct. 19, 2020, 7 pages.
Zhang, Development of an Epitope-based Competitive ELISA for the Detection of Antibodies against Tibetan Peste des Petits Ruminants Virus, Intervirology 56(1):55-9 (2013).
Office Action for European Application No. 18751757.8 dated Dec. 17, 2025 (6 pages).

*Primary Examiner* — Galina M. Yakovleva

(74) *Attorney, Agent, or Firm* — David W. Staple; Casimir Jones, S.C.

(57) ABSTRACT

Provided herein are compositions, kits, and methods for performing analyte detection immunoassays.

11 Claims, 6 Drawing Sheets

Assay detection range: 10ng/ml - ~1.0 ug/ml
(Upper detection limit can be extended to 100ug/ml)

Assay detection range: 10pg/ml ~10 ng/ml

ANALYTE DETECTION IMMUNOASSAY

CROSS REFERENCE TO RELATED APPLICATIONS

The present application is a divisional of U.S. patent application Ser. No. 15/892,557, filed Feb. 9, 2018, now allowed, which claims the benefit of U.S. Provisional Patent Application Ser. No. 62/456,906, filed Feb. 9, 2017, each of which is incorporated by reference in its entirety.

FIELD

Provided herein are compositions, kits, and methods for performing analyte detection immunoassays.

BACKGROUND

Ligand binding assays/immunoassays are routinely used for analyte detection in research, diagnostics, therapeutic development, environmental monitoring, etc., but have significant limitations.

SUMMARY

Provided herein are compositions, kits, and methods for performing analyte detection immunoassays.

In some embodiments, provided herein are methods for detection/quantification of a target analyte (e.g., an antibody) in a sample, comprising: (a) exposing a surface displaying immobilized capture agents to the sample in the presence a labeled competitor; wherein the competitor and target analyte are both capable of binding to the capture agents; (b) measuring signal from the labeled competitor, wherein the signal from the labeled competitor is (A) proportional to the amount of labeled competitor bound to the capture agents and (B) inversely proportional to the amount of target analyte in the sample; (c) exposing the surface to a labeled detection agent, wherein the labeled detection agent is capable of binding to the target analyte but not to the labeled competitor; and (d) measuring signal from the labeled detection agent, wherein the signal from the labeled detection agent is (A) proportional to the amount of labeled detection agent bound to the target analyte and (B) proportional to the amount of target analyte in the sample. In some embodiments, steps (a)-(d) are performed on the same target analytes, in the same sample, and on the same physical location (e.g., same well, same spot on a plate, etc.). In some embodiments, a known amount (e.g., concentration) of labeled competitor is used. In some embodiments, a sample comprises an unknown amount (e.g., concentration) of target analyte. In some embodiments, methods further comprise comparing the signal from the labeled competitor and/or the signal from the labeled detection agent to reference values prepared using known amounts of target analyte (e.g., in the assays described herein) to determine the amount of target analyte in the sample. In some embodiments, methods further comprise determining a ratio of the signal from the labeled competitor and the signal from the labeled detection agent. In some embodiments, methods further comprise comparing the dimensionless quantity to reference ratios prepared using known amounts of target analyte to determine the amount of target analyte in the sample. In some embodiments, the labeled competitor and the labeled detection agent comprise detectably different labels (e.g., reporter enzymes, fluorophores, radioisotopes, nanoparticles, etc.). In some embodiments, the labeled competitor and the labeled detection agent comprise the same labels, the method further comprising a step between steps (b) and (c) of administering an inhibitor of the label, such that the signal from step (b) is not substantially detected in step (d). In some embodiments, the label of the labeled competitor comprises an enzyme with detectable activity. In some embodiments, the inhibitor inhibits the detectable activity of the enzyme. In some embodiments, the inhibitor prevents substrate association with the enzyme. In some embodiments, the inhibitor prevents substrate turnover by the enzyme. In some embodiments, the target analyte is a target antibody. In some embodiments, the capture agent displays an epitope for the target antibody. In some embodiments, the labeled competitor comprises an antibody fragment (e.g., $F(ab)_2$, ScFc, Fab, etc.) or an antibody mimetic molecule (e.g., DARPin® molecules, AFFIBODY® molecules, aptamers, NANOBODY® molecules, etc.). In some embodiments, the labeled competitor lacks an Fc region. In some embodiments, the labeled competitor comprises an antibody fragment or antibody mimetic molecule that is capable of binding the epitope for the target antibody. In some embodiments, the labeled competitor is fused to a bioluminescent reporter. In some embodiments, the $F(ab)_2$ fragment is fused to a bioluminescent reporter. In some embodiments, the bioluminescent reporter is a variant of Oplophorus luciferase, e.g., NANOLUC® luciferase. In some embodiments, the detection agent comprises an anti-Fc antibody, anti-Fc antibody fragment, or anti-Fc antibody mimetic molecule that is capable of binding to the Fc portion of the target antibody but not to the competitor (e.g., $F(ab)_2$ fragment), which lacks an Fc region.

In some embodiments, provided herein are systems comprising reagents for performing an immunoassay for the detection of a target analyte (e.g., antibody) comprising: (a) a surface displaying capture agents that the target analyte is capable of binding; (b) a competitor comprising a first detectable label and capable of binding to the capture agents: (c) a detection agent comprising a second detectable label and capable of binding to the target analyte but not to the competitor. In some embodiments, the surface is the interior of a microwell. In some embodiments, the target analyte is a target antibody. In some embodiments, the target antibody is a therapeutic antibody. In some embodiments, the capture agent comprises an epitope of the target analyte (e.g., antibody). In some embodiments, the capture agent is an antigen of the target analyte (e.g., antibody). In some embodiments, the capture agent is immobilized on the surface by a covalent linkage, by noncovalent linkage (e.g., biotin/streptavidin association, adsorption), or through the binding to an antibody that is immobilized on the surface and binds a separate epitope of the capture agent than the target analyte (e.g., antibody). In some embodiments, the competitor comprises an antibody, antibody fragment, or antibody mimetic molecule that is capable of binding the epitope for the target analyte (e.g., antibody). In some embodiments, the competitor is antibody fragment or antibody mimetic molecule that lacks an Fc region. In some embodiments, the competitor comprises an ScFv, Fab, $F(ab)_2$, or other fragment that is capable of binding the epitope for the target antibody. In some embodiments, the first detectable label is selected from a fluorescent dye, an enzyme with detectable activity, and a fluorescent protein. In some embodiments, the first detectable label is an enzyme, and the detectable activity is luminescence. In some embodiments, the detection agent comprises an anti-Fc antibody, anti-Fc antibody fragment, or anti-Fc antibody mimetic that is capable of binding the Fc region of the target antibody but not to the Fab region (e.g., not to a $F(ab)_2$ fragment or other fragment or molecule lacking an Fc region). In some embodiments, the second detectable label is selected from a fluorescent dye, an enzyme with detectable activity, and a fluorescent protein. In some embodiments, the second detectable label is an enzyme, and the detectable activity is luminescence. In some embodiments, the first label and the second label are detectably different labels. In some embodiments, the first label and the second label are the same label, and the system further comprises an inhibitor of the label. In some embodiments, the first label and second label are enzymes. In some embodiments, the inhibitor inhibits the activity of the enzymes. In some embodiments, the inhibitor prevents an enzyme substrate from accessing an active site of the enzyme. In some embodiments, the inhibitor prevents an enzyme substrate from turnover.

In some embodiments, provided herein are methods of detecting/quantifying a target antibody in a sample comprising: (a) exposing a surface displaying immobilized capture agents to the sample in the presence a labeled competitor, wherein the capture agents comprise an epitope for the target antibody, and wherein the competitor comprises an antibody fragment lacking an Fc region (e.g., a $F(ab)_2$ fragment) or an antibody mimetic (e.g., DARPin® molecules, AFFIBODY® molecules, aptamer, NANOBODY® molecules, etc.) and a first detectable label and is capable of binding to the epitope for the target antibody; (b) measuring signal from the first detectable label, wherein the signal from the first detectable label is (A) proportional to the amount of labeled competitor bound to the capture agents and (B) inversely proportional to the amount of target antibody in the sample; and (c) exposing the surface to a labeled detection agent, wherein the labeled detection agent comprises an anti-Fc antibody, anti-Fc antibody fragment or anti-Fc antibody mimetic and a second detectable label, and wherein the detection agent is capable of binding to the target antibody but not to the labeled competitor, wherein the signal of the second detectable label is differentiable from the signal of the first detectable label; and (d) measuring the signal from the second detectable label, wherein the signal from the second detectable label is (A) proportional to the amount of labeled detection agent bound to the target analyte and (B) proportional to the amount of target analyte in the sample.

In some embodiments, provided herein are methods of detecting/quantifying a target antibody in a sample comprising: (a) exposing a surface displaying immobilized capture agents to the sample in the presence a labeled competitor, wherein the capture agents comprise an epitope for the target antibody, and wherein the competitor comprises an antibody fragment that lacks an Fc region (e.g., $F(ab)_2$ fragment) or antibody mimetic and a detectable label and is capable of binding to the epitope for the target antibody; (b) measuring a signal from the first detectable label, wherein the signal from the first detectable label is (A) proportional to the amount of labeled competitor bound to the capture agents and (B) inversely proportional to the amount of target antibody in the sample: (c) administering an inhibitor of the detectable label, wherein the inhibitor prevents subsequent signal detection from the detectable label of the labeled competitor; (d) exposing the surface, with the inhibited labeled competitor and the target antibody bound to the capture agents, to a labeled detection agent, wherein the labeled detection agent comprises an anti-Fc antibody, fragment or mimetic and the detectable label and is capable of binding to the target analyte but not to the labeled competitor; and (e) measuring a second signal from the detectable label, wherein the second signal from the detectable label is (A) proportional to the amount of labeled detection agent bound to the target antibody and (B) proportional to the amount of target antibody in the sample. In some embodiments, methods further comprise a step between steps (c) and (d) of washing away unbound inhibitor in the sample.

BRIEF DESCRIPTION OF THE DRAWINGS

FIG. 1A shows the detection of labeled competitor, FIG. 1B shows the detection of labeled detection reagent.

Definitions

Figure 1A:
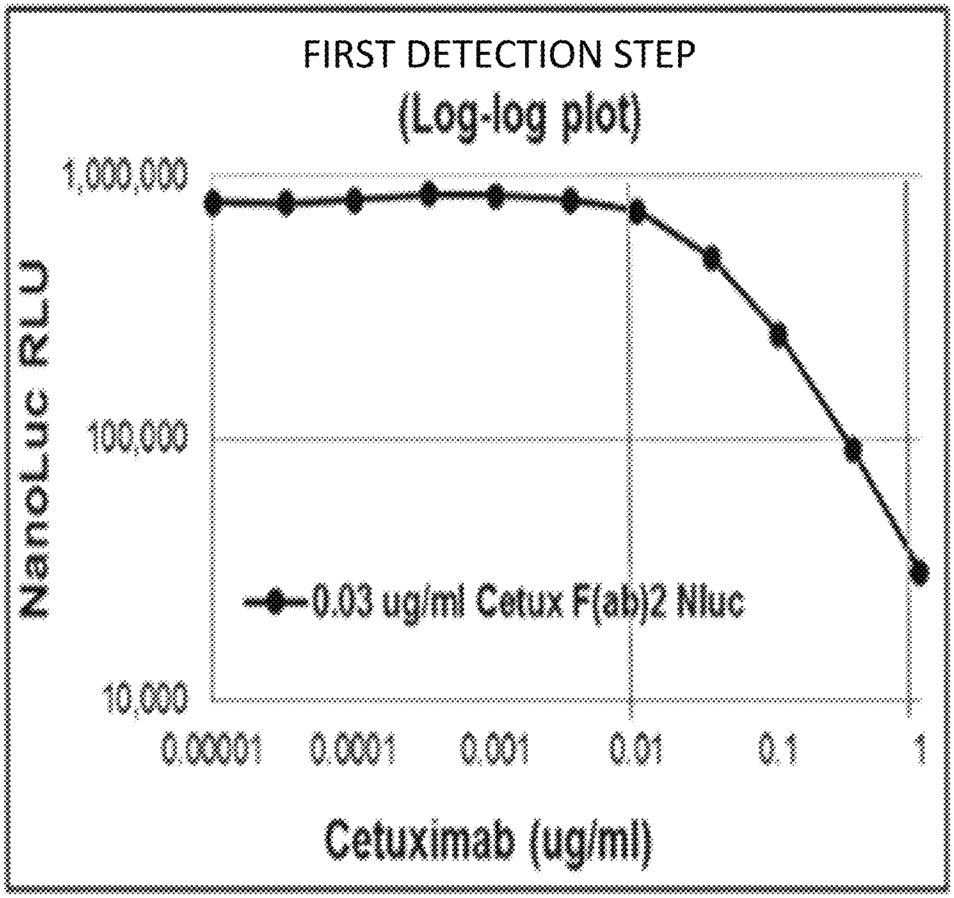
FIGS. 1A-B. Results of two-reporter immunoassay for detection of Cetuximab.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms “a”, “an” and “the” include plural reference unless the context clearly dictates otherwise. Thus, for example, reference to “an analyte” is a reference to one or more analytes and equivalents thereof known to those skilled in the art, and so forth.

As used herein, the term “comprise” and linguistic variations thereof denote the presence of recited feature(s), element(s), method step(s), etc. without the exclusion of the presence of additional feature(s), element(s), method step(s), etc. Conversely, the term “consisting of” and linguistic variations thereof, denotes the presence of recited feature(s), element(s), method step(s), etc. and excludes any unrecited feature(s), element(s), method step(s), etc., except for ordinarily-associated impurities. The phrase “consisting essentially of” denotes the recited feature(s), element(s), method step(s), etc. and any additional feature(s), element(s), method step(s), etc. that do not materially affect the basic nature of the composition, system, or method. Many embodiments herein are described using open “comprising” language. Such embodiments encompass multiple closed “consisting of” and/or “consisting essentially of” embodiments, which may alternatively be claimed or described using such language.

As used herein, the term "sample" is used herein in its broadest sense. It is meant to include: a specimen, culture, lysate, purified analyte, purified enzyme, purified analyte in buffer, etc. It includes a prepared solution or mixture, and both biological and environmental collections. Biological samples may take the form of a fluid or solid, may be obtained from any suitable biological source (e.g., animal, including human, microbiological, etc.), and may include blood (e.g., whole blood, leukocytes, peripheral blood mononuclear cells, buffy coat, plasma, and serum), sputum, tears, mucus, nasal washes, nasal aspirate, breath, urine, semen, saliva, peritoneal washings, ascites, cystic fluid, meningeal fluid, amniotic fluid, glandular fluid, lymph fluid, nipple aspirate, bronchial aspirate, bronchial brushing, synovial fluid, joint aspirate, organ secretions, cells, a cellular extract, and cerebrospinal fluid. Environmental samples include environmental material such as surface matter, soil, plants, and water. These examples are not to be construed as limiting the sample types applicable to the present invention. Samples also include processed or otherwise separated fractions of all of the preceding. For example, a blood sample can be fractionated into serum, plasma, or into fractions containing particular types of blood cells, such as red blood cells or white blood cells (leukocytes). In some embodiments, a sample can be a combination of samples from an individual, such as a combination of a tissue and fluid sample. The term "sample" may also include materials containing homogenized solid material, such as from a stool sample, a tissue sample, or a tissue biopsy; and materials derived from a tissue culture or a cell culture. A sample may be processed in any suitable manner (e.g., filtered, diluted, pooled, fractionated, concentrated, etc.) after being obtained/provided.

As used herein, the term "analyte" refers to a molecular constituent of a sample (e.g., biological sample, environmental sample, etc.) that can be detected, quantified, and/or analyzed by appropriate methods (e.g., immunoassay). Analytes may be naturally occurring substances (e.g., obtained/provided from a biological or environmental sample) or artificial substances (e.g., synthesized). In some embodiments, an analyte may be an antibody (e.g., therapeutic antibody), antibody fragment, antigenic molecule, etc.

As used herein, the term "labeled detection agent" refers to an antibody, antibody fragment, or antibody mimetic molecule that binds to a target analyte (e.g., Fc region of target antibody), but not to a labeled competitor (e.g., which lacks an Fc region) and comprises a detectable label, the label being selected from the list including but not limited to, an enzyme, nucleic acid, radioisotope, fluorescent molecule, nanoparticle, or combination thereof.

As used herein, the term "labeled competitor" refers to an antibody, antibody fragment, or antibody mimetic molecule that binds to a capture agent (e.g., immobilized on a surface) but is structurally non-identical to the target analyte (e.g., lacks an Fc region, is an antibody mimetic, comprises a blocking moiety, etc.).

As used herein, the term 'immunoassay' refers to antibody-antigen binding assay and includes, but is not limited to, ELISA, ligand binding assay, sandwich immunoassay, indirect immunoassay, radioimmunoassay, Western Blot detection, Dot Blot assay, bead based immunoassay etc.

As used herein, the term "antibody" refers to a whole antibody molecule or a fragment thereof (e.g., fragments such as Fab, Fab', and $F(ab')_2$), unless specified otherwise. Embodiments referring to "an antibody" encompass multiple embodiments including "a whole antibody" and fragments of the antibody, which may alternatively be claimed or described using such language.

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, VHI, and three constant regions, $C_{H1}$, $C_{H2}$, and $C_{H3}$. The $V_H$ domain is at the amino-terminus of the heavy chain, and the $C_{H3}$ domain is at the carboxy-terminus. In a native antibody, a light chain comprises a variable region, $V_L$, and a constant region, $C_L$. The variable region of the light chain is at the amino-terminus of the light chain. In a native antibody, the variable regions of each light/heavy chain pair typically form the antigen binding site. The constant regions are typically responsible for effector function.

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. H3, for example, in certain instances, can be as short as two amino acid residues or greater than 26. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia, C., and Lesk, A. M. (1987) J. Mol. Biol. 196:901-917; or Chothia, C. et al. Nature 342:878-883 (1989). In the present application, the term "CDR" refers to a CDR from either the light or heavy chain, unless otherwise specified.

As used herein, the term "heavy chain" refers to a polypeptide comprising sufficient heavy chain variable region sequence to confer antigen specificity either alone or in combination with a light chain.

As used herein, the term "light chain" refers to a polypeptide comprising sufficient light chain variable region sequence to confer antigen specificity either alone or in combination with a heavy chain.

As used herein, when an antibody or other entity "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope, which is distinguished from entities using a desired assay or measurement apparatus. Typically, it means binding affinity having a binding constant ($K_a$) of at least $10^7$ $M^{-1}$ (e.g., $>10^7$ $M^{-1}$, $>10^8$ $M^{-1}$, $>10^9$ $M^{-1}$, $>10^{10}$ $M^{-1}$, $>10^{11}$ $M^{-1}$, $>10^{12}$ $M^{-1}$, $>10^{13}$ $M^{-1}$, etc.). In certain such embodiments, an antibody is capable of binding different antigens so long as the different antigens comprise that particular epitope. In certain instances, for example, homologous proteins from different species may comprise the same epitope.

As used herein, the term "antibody fragment" refers to a portion of a full-length antibody, including at least a portion antigen binding region or a variable region. Antibody fragments include, but are not limited to, Fab, Fab', $F(ab')_2$, Fc, Fv, scFv, Fd, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion, pepsin, and Ides digestion of antibody) produced by recombinant DNA techniques, or chemical polypeptide synthesis.

For example, a "Fab" fragment comprises one light chain and the $C_{H1}$ and variable region of one heavy chain. The heavy chain of a Fab molecule cannot form a disulfide bond with another heavy chain molecule. A "Fab" fragment comprises one light chain and one heavy chain that comprises additional constant region, extending between the $C_{H1}$ and $C_{H2}$ domains. An interchain disulfide bond can be formed between two heavy chains of a Fab' fragment to form a "$F(ab')_2$" molecule. A $F(ab)_2$ lacks an Fc region.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen.

Other antibody fragments will be understood by skilled artisans.

An "anti-Fc" antibody, antibody fragment, or antibody mimetic molecule binds to the Fc portion of an antibody or antibody fragment. An anti-Fc antibody or antibody fragment does not bind to an F(ab) or $F(ab)_2$ antibody fragment.

DETAILED DESCRIPTION

Immunoassays (e.g., Enzyme linked immunosorbent assays (ELISA), Ligand Binding Assays (LBA), etc.), are used for analyte detection in research, diagnostics, therapeutic development, environmental monitoring, etc. Provided herein are compositions, kits, and methods for performing analyte detection immunoassays.

In some embodiments, a sample comprising an analyte is exposed to reagents for performing an immunoassay. In some embodiments, the same sample and/or analytes are used for the entire assay (e.g., first and second detection steps). In some embodiments, the entire assay (e.g., capture of target analyte, binding of labeled competitor, label inhibition, wash steps, binding of detection agent, detection steps, etc.) are performed in/on the same physical location (e.g., the same spot on a plate or slide, within the same microwell, etc.). In some embodiments, a wash step is performed between steps (e.g., following a first detection step, following label inhibition, following a binding step, etc.). In some embodiments, complex instrumentation, such as microfluidics (See, e.g., U.S. Pub. No. 2016/0161474; incorporated by reference in its entirety) and/or electrode arrays (See, e.g., U.S. Pat. No. 7,858,321; incorporated by reference in its entirety) are not required and/or utilized in the performance of all or a portion of the assay. In some embodiments, a single detectable label or type of detectable label (e.g., fluorescent dye, bioluminescent protein (e.g., luciferase), etc.) is used for all detection steps of the assay. In some embodiments, different fluorescent dyes are not used for the separate detection steps of the assay (See, e.g., Hartmann et al. Clinical Chem. 54:6, 956-963 (2008); incorporated by reference in its entirety). In other embodiments, detectably-different labels are used for the separate detection steps of the assay. In some embodiments, the results of each detection step of the assay are considered separately (e.g., a comparison and/or ratio of the signals from first and second detection steps is not performed or generated). In some embodiments, the results of each detection step of the assay are combined (e.g., by taking a ratio).

In some embodiments, a capture agent is bound to a surface (e.g., well, plate, bead, etc.) and the surface is then exposed to a sample comprising the analyte and a labeled competitor of the analyte. In a typical response (See, e.g., FIG. 1A), signal from the label decreases with increasing concentration of analyte, as the labeled competitor is competed off the surface. Comparison to reference values determined using a known amount of analyte allows for quantification of the amount of analyte present in a sample.

Following the above detection step, in some embodiments, the reaction mixture is prepared for a second detection step. In some embodiments, an inhibitor of the label used in the detection step described above is added to the sample (e.g., an agent that significantly reduces (e.g., 50% signal reduction, 60% signal reduction, 70% signal reduction, 80% signal reduction, 90% signal reduction, 95% signal reduction, 99% signal reduction, 99.9% signal reduction, 99.99% signal reduction, or more or ranges therebetween) the signal from the label in the reaction mixture, thereby allowing an identical label to be used in a second detection step in the same reaction mixture. In some embodiments, the label inhibitor is followed by a wash step to remove unbound inhibitor. In some embodiments, the label inhibitor binds the label and remains bound to the label during subsequent steps, thereby preventing signal from residual label from the first detection from being detected during a subsequent detection step. In some embodiments, no inhibitor is added between first and second detection steps. In some embodiments, a wash step is performed whether or not inhibitor is added.

In some embodiments, to perform a second detection step, a detection agent is added to the sample. In some embodiments, a detection agent comprises a detectable label and binds specifically to the analyte, but not the competitor. In some embodiments, the detection agent is an antibody, antibody fragment, or antibody mimetic molecule. In some embodiments in which the analyte is an antibody, the detection agent is a labeled anti-Fc antibody, labeled anti-Fc antibody fragment, or labeled anti-Fc antibody mimetic molecule. In such embodiments, the detection agent is capable of binding the Fc portion of the analyte, but not to a competitor that does not comprise an Fc portion (e.g., an antibody fragment lacking an Fc region (e.g., a $F(ab)_2$ fragment), an antibody mimetic molecule, etc.). In some embodiments, a competitor lacks an Fc portion. In other embodiments, the competitor comprises a blocking moiety not present on the analyte that prevents the detection agent from binding the competitor. In some embodiments, the detection agent comprises the same label as the labeled competitor (e.g., embodiments in which an inhibitor of the label is administered between the detection steps). In some embodiments, the detection agent comprises a different label than the labeled competitor (e.g., embodiments in which an inhibitor of the label is not administered between detection steps).

Embodiments herein find use in the detection and/or quantification of analytes in a sample. Assays, devices (e.g., fluorimeter, luminometer, surface, etc.), and reagents (e.g., capture agent(s), analyte competitor(s), label(s), label inhibitor(s), wash solution(s), detection agent(s), buffer, etc.) are provided for the detection/quantification/assessment of any type of analyte. Exemplary analytes include small molecules, peptides, proteins, antibodies, carbohydrates, lipids, etc. In some embodiments, samples comprising an analyte of interest are provided. In some embodiments, a sample comprising an analyte of interest is prepared and/or processed (e.g., filtered, concentrated, diluted, centrifuged, etc.). In some embodiments, an analyte of interest is added to a sample. Any analyte for which suitable capture agent, competitor, and/or detection agent are available and/or are designed/prepared may find use in embodiments herein.

In some embodiments, an analyte is an antibody or antibody fragment. In such embodiments, a capture agent is typically an antigen for the antibody or antibody fragment or another agent displaying an epitope for the antibody or antibody fragment. In other embodiments, a capture agent is an antibody or antibody fragment that binds to the analyte (e.g., an antibody analyte, a non-antibody analyte, etc.).

In some embodiments, a capture agent is any small molecule, peptide, polypeptide, nucleic acid, antibody, antibody fragment, etc. that is capable of binding and forming a stable association with the analyte (e.g., stable under assay conditions). In some embodiments, a capture agent is an antigen (e.g., when the target analyte is an antibody). In some embodiments, a capture agent is capable of being immobilized (e.g., covalently, stable non-covalent immobilization, etc.) onto a surface. In some embodiments, a capture agent comprises an immobilization moiety that facilitates immobilization of the capture agent to, for example, a surface. In some embodiments, the immobilization moiety is a reactive functional group that facilitates covalent interaction with a moiety displayed on the surface. In some embodiments, a capture agent comprises a capture moiety (e.g., antigen-recognition moiety, epitope-display moiety, analyte-binding moiety, etc.) and an immobilization moiety (e.g., HALOTAG® protein or ligand (See, e.g., U.S. Pat. Nos. 7,238,842; 7,425,436; incorporated by reference in their entireties), biotin or streptavidin, etc.). In some embodiments, the immobilization moiety is an affinity molecule (e.g., streptavidin or biotin) that facilitates noncovalent association with a moiety displayed on the surface (e.g., biotin or streptavidin).

In some embodiments, the assays described herein are performed on a surface. Any suitable surface to which a capture agent may be immobilized will find use in embodiments herein. In some embodiments, a surface is any solid or stationary material to which a capture agent is attached. Examples of surfaces include microscope slides, microarrays, wells of microtiter plates, coverslips, beads, particles (e.g., nanoparticles, microparticles, quantum dots, etc.), resin, cell culture flasks, as well as many other suitable items. In some embodiments, a surface is coated and/or functionalized to facilitate the attachment of a capture agent. In some embodiments, a surface displays (e.g., with or without specific functionalization, via adsorption from solution, etc.) one or more moieties to facilitate immobilization of a capture agent to the surface. For example, in some embodiments, a surface displays HALOTAG® protein or ligand and a capture agent comprising an immobilization moiety that displays the complement HALOTAG® protein or ligand component. As another example, in some embodiments, a surface displays biotin and/or streptavidin and a capture agent comprises an immobilization moiety that displays the complement biotin/streptavidin component. In some embodiments, the surface and/or immobilization moiety of the capture agent displays an antibody or antibody fragment and the other displays the antigen/epitope for that antibody or antibody fragment. Any suitable agents/moieties for immobilization of a capture agent to a surface are within the scope of embodiments herein.

In some embodiments, following immobilization of the capture agent to the surface, the remaining exposed surface is blocked to prevent non-specific binding. In some embodiments, blocking comprises immobilizing an inert agent to the surface. In some embodiments, blocking comprises neutralizing or inactivating potentially-reactive sites on the surface.

In some embodiments, a competitor (analyte competitor) is an agent that binds to the capture agent with a similar affinity or strength of interaction as the analyte. In some embodiments, a competitor comprises a detectable label or detectable moiety. In certain embodiments in which the analyte is an antibody or antibody fragment, a competitor is a labeled antibody, antibody fragment, or antibody mimetic molecule that binds to the same antigen/epitope as the analyte. Compositions and methods for labeling antibodies, antibody fragments, and/or antibody mimetic molecules with diverse categories of detectable labels are understood in the field. In some embodiments in which the capture agent is an antibody or antibody fragment, the competitor displays the same antigen/epitope as the analyte. In other embodiments, for example, when the analyte is a small molecule, peptide, protein, carbohydrate, lipid, etc., the competitor displays a competition moiety that is capable of binding to (or being bound by) the capture agent with similar affinity to the analyte. In some embodiments, the affinity of the competitor for the capture agent is sufficient such that at low concentration of competitor relative to the analyte, the majority (e.g., 90%, 91%, 92%, 93%, 94%, 95%, 96%, 97%, 98%, 99%, 99.9%, 99.99%, 99.999%, or more, or ranges therebetween) of the capture agents are bound to analyte. However, as the relative concentration of competitor to analyte increases, the competitor competes the analyte off the capture agents (See, e.g., FIG. 2). In some embodiments, the competitor is an antibody fragment (e.g., $F(ab)_2$, ScFc, Fab, etc.) or an antibody mimetic molecule (e.g., DARPin® molecules, AFFIBODY® molecules, aptamers, NANOBODY® molecules, etc.) that is capable of binding the capture agent, but is structurally distinct from the target analyte (e.g., comprises a blocking moiety, lacks an Fc region, etc.). In some embodiments, the competitor is an antibody fragment (e.g., $F(ab)_2$. ScFc, Fab, etc.) or an antibody mimetic molecule (e.g., DARPin® molecules, AFFIBODY® molecules, aptamers, NANOBODY® molecules, etc.) that lacks an Fc region but is capable of binding the epitope for the target antibody.

In some embodiments, a competitor comprises a detectable label. Any label that facilitates the monitoring of the competition between analyte and competitor finds use in embodiments herein. In some embodiments, a label is, for example, an enzyme (e.g., akaline phosphatase (AP) and horseradish peroxidase (HRP), etc.), a radioactive label (e.g., radionuclides), a chromophore (e.g., a dye or particle that imparts a detectable color), a luminescent moiety (e.g., bioluminescent (e.g., photoprotein, luciferase (e.g., *renilla*, firefly, NANOLUC® luciferase (See, e.g., U.S. Pat. No.

8,859,220; incorporated by reference in its entirety) etc.), etc.), phosphorescent or chemiluminescent label), or a fluorescent moiety (e.g., fluorescent protein (e.g. green fluorescent protein (GFP), enhanced GFP (EGFP), yellow fluorescent protein (YFP), cyan fluorescent protein (CFP), etc.), fluorophore (e.g., xanthene derivatives, cyanine derivatives, etc.). In some embodiments, the detectable moiety is a small molecule, peptide, polypeptide, nucleic acid (e.g., DNA), nanoparticles (e.g., Quantum Dots), or protein that is conjugated or fused directly or indirectly (e.g., via a suitable linker) to a moiety that binds the capture agent).

In some embodiments, a competitor comprises a competitive moiety (e.g., the portion of the competitor that mimics analyte binding to the capture agent) and a detectable moiety (e.g., detectable label). In some embodiments, the competitive moiety and the detectable moiety are conjugated directly or indirectly. In some embodiments, the competitive moiety and the detectable moiety are conjugated by known methods. In some embodiments, the competitive moiety and the detectable moiety are conjugated by a linker moiety. In some embodiments, the competitive moiety and the detectable moiety are polypeptides (e.g., antibody fragment and luciferase) and are part of a single fusion protein (e.g., optionally comprising a linker peptide between the competitive moiety and the detectable moiety). Any suitable linkers may find use in embodiments herein. In some embodiments in which the competitive moiety and/or the detectable moiety are not polypeptides (e.g., fluorescent dye as detectable moiety, small molecule as competitive moiety), a linker may be a non-peptide linker (e.g., alkyl linker, heteroalkyl linker, carbamate linker, PEG linker, etc.).

In some embodiments, an analyte is an antibody or antibody fragment (e.g., antibody fragment comprising all or a portion of an Fc), and a competitor is a labeled antibody fragment lacking all or a portion of an Fc region. In some embodiments, a competitor is a labeled $F(ab)_2$ fragment.

In some embodiments of the systems and methods described herein, an inhibitor of the label on the analyte competitor is employed to reduce and/or eliminate the signal from the label following completion of the first detection step and and prior to the second detection step. In some embodiments, in which the label is a fluorescent label, the inhibitor is a quencher of that fluorofore. In some embodiments, particularly in which the detectable label is an enzyme, the inhibitor binds to the detectable label and prevents the association of a substrate or other necessary factor (e.g., ATP) to the detectable label. In some embodiments, an inhibitor is a modified substrate that cannot participate or converted by the enzyme to a reaction product in a signal (e.g., light) producing reaction. In some embodiments, the detectable label is a luciferase (e.g., firefly luciferase, Oplophorus luciferase (e.g. NANOLUC® luciferase), etc.) and the inhibitor is a substrate analog (e.g., a luciferin analog or a coelenterazine analog) that cannot be converted into a reaction product in a light producing reaction (e.g., an oxoluciferin or a coelenteramide). In some embodiments, the detectable label is a variant of an Oplophorus luciferase (e.g., NANOLUC® luciferase), and the inhibitor inhibits the activity of the variant of an Oplophorus luciferase thereby inhibiting its luciferase activity (see for example U.S. Pat. App. Nos. Ser. No. 15/192,420 and 62/439,600; incorporated by reference in their entireties). In some embodiments, an inhibitor binds stably, covalently, and/or irreversibly to the detectable label. In some embodiments, particularly in which the detectable label is a fluorophore, an inhibitor is a quencher of the detectable signal (e.g., fluorescence) from the label. In some embodiments, the inhibitor inhibits enzymatic activity of the label, e.g., antibody or small molecule.

In some embodiments, a wash step and wash reagents are employed between the first and second detection steps of the assays described herein. In some embodiments, the wash step removes unbound analyte and/or competitor. In some embodiments, the wash step removes excess inhibitor. In some embodiments, wash reagents comprise water, buffer (s), salts, detergents, surfactants, etc. In some embodiments, a wash reagents comprise any components that facilitate the removal of unwanted contaminants (e.g., components of the assay that have already been used and are not necessary/desired for subsequent assay steps) without disrupting the assay components (e.g., without de-immobilizing the capture agent from the surface, without disassociating the analyte and/or competitor from the capture agent, without disassociating the inhibitor from the detectable label of the competitor, etc.).

In some embodiments, the assays described herein utilize a detection agent. In some embodiments, a detection agent is any agent that binds to the analyte (e.g., an analyte that is bound to a capture agent), but doesn't bind to the analyte competitor. In some embodiments, the detection agent is labeled. Like the label on the competitor, any label that facilitates the monitoring of the binding of the detection agent to the captured analyte finds use in embodiments herein. In some embodiments, a label is, for example, an enzyme (e.g., akaline phosphatase (AP) and horseradish peroxidase (HRP), etc.), a radioactive label (e.g., radionuclides), a chromophore (e.g., a dye or particle that imparts a detectable color), a luminescent moiety (e.g., bioluminescent (e.g., photoprotein, luciferase (e.g., *renilla*, firefly, NANOLUC® luciferase (See, e.g., U.S. Pat. No. 8,859,220; incorporated by reference in its entirety) etc.), etc.), phosphorescent or chemiluminescent label), or a fluorescent moiety (e.g., fluorescent protein (e.g. green fluorescent protein (GFP), enhanced GFP (EGFP), yellow fluorescent protein (YFP), cyan fluorescent protein (CFP), etc.), fluorophore (e.g., xanthene derivatives, cyanine derivatives, etc.). In some embodiments, the detectable moiety is a small molecule, peptide, polypeptide, or protein that is conjugated or fused directly or indirectly (e.g., via a suitable linker) to a moiety that binds the capture agent). In some embodiments, the detection agent label and the competitor label are the same (e.g., NANOLUC® luciferase). In such embodiments, an inhibitor is employed between the first and second detection steps of the assay. In some embodiments, the different labels are employed on the competitor and detection agents of the assays described herein. In some embodiments, the use of separate labels allows the two portions of the assay to be performed without the use of label inhibitor.

In some embodiments, a detection agent comprises an analyte-binding moiety (e.g., the portion of the detection agent that binds to the analyte when the analyte is bound to the capture agent) and a detectable moiety (e.g., detectable label). In some embodiments, the analyte-binding moiety and the detectable moiety are conjugated directly or indirectly. In some embodiments, the analyte-binding moiety and the detectable moiety are conjugated by known methods. In some embodiments, the analyte-binding moiety and the detectable moiety are conjugated by a linker moiety. In some embodiments, the analyte-binding moiety and the detectable moiety are polypeptides (e.g., antibody fragment and luciferase) and are part of a single fusion protein (e.g., optionally comprising a linker peptide between the analyte-binding moiety and the detectable moiety). Any suitable linkers may find use in embodiments herein. In some embodiments in which the analyte-binding moiety and/or the detectable moiety are not polypeptides (e.g., fluorescent dye as detectable moiety, small molecule as analyte-binding moiety), a linker may be a non-peptide linker (e.g., alkyl linker, heteroalkyl linker, carbamate linker, PEG linker, etc.).

In some embodiments, the detection agent is a labeled antibody that recognizes a moiety that is present on the analyte, but is absent from the competitor. In some embodiments, the competitor comprises a blocking moiety that prevents the detection agent from binding to the competitor. In some embodiments, the label on the competitor prevents the detection agent from binding to the competitor. In some embodiments, the analyte is an antibody or antibody fragment comprising all or a portion of an Fc, the competitor is an antibody fragment lacking all or a portion of the Fc, and the detection agent is an anti-Fc antibody or antibody fragment that binds to the analyte but not to the competitor.

In some embodiments, by performing the immunoassays described herein using standards and/or samples comprising known amounts of analyte, calibration curves are generated. In some embodiments, assays described herein are capable of generating calibration curves spanning a wide dynamic range. In some embodiments, using these calibration curves, assay results for samples comprising unknown amounts of analyte are compared to one or both of the reference calibration curves (e.g., calibration curves for the first and second detection steps) to identify the amount of analyte present in the sample. In other embodiments, a dimensionless quantity is calculated by taking a ratio of the signals from the first and second detection steps of the assay (see FIG. 4); this dimensionless quantity is plotted against the analyte concentration. The resulting single plot covers the entire dynamic range obtained from the two detection steps. In a typical graph resulting from the combination of the two detection steps, an increase in x-value corresponds to an increase in analyte concentration, making analysis more intuitive.

Certain processes and methods described herein (e.g., data acquisition, data analysis, communication, etc.) are performed by (or cannot be performed without) a computer, processor, software, and/or other device. All or a portion of the methods described herein may be computer-implemented methods, and one or more portions of a method sometimes are performed by one or more processors. In some embodiments, an automated method is embodied in software, processors, peripherals and/or an apparatus comprising the like. As used herein, software refers to computer readable program instructions that, when executed by a processor, perform computer operations, as described herein. In some embodiments, reference values, are stored in a memory element (e.g., comprising a database), and the reference values are accessed by a processor to compare to experimentally acquired data. In some embodiments, calculations are performed by processors, computers, software, etc. to acquire data using the methods described herein (e.g., measure signal from detectable labels), process the data (e.g., plot the data, calculate ratios, regression analysis, calculate derivatives or integrals of data, etc.), compare data to stored reference values (e.g., thresholds, concentrations of analyte, etc.), etc.

EXPERIMENTAL

Experiments conducted during development of embodiments herein to demonstrate the feasibility and utility of the immunoassays described herein.

Example 1

Two-Reporter Immunoassay

Figure 1B:
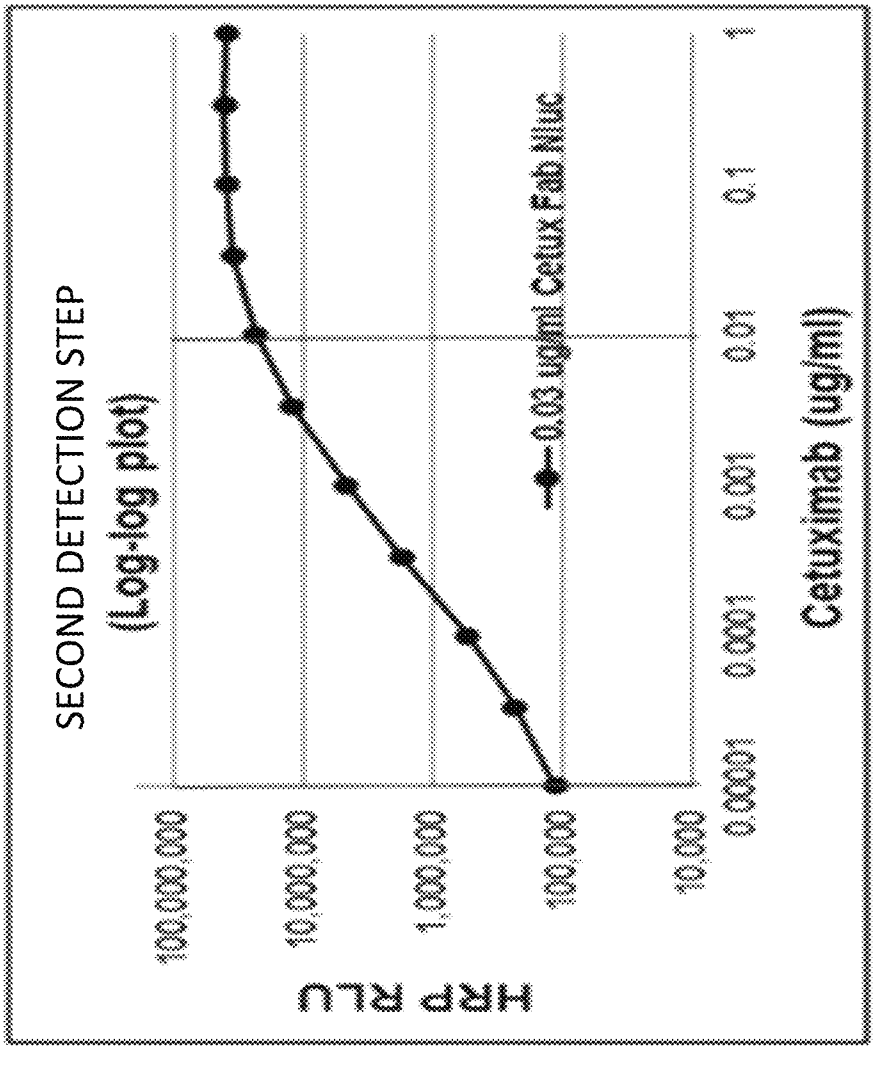
Figure 2:
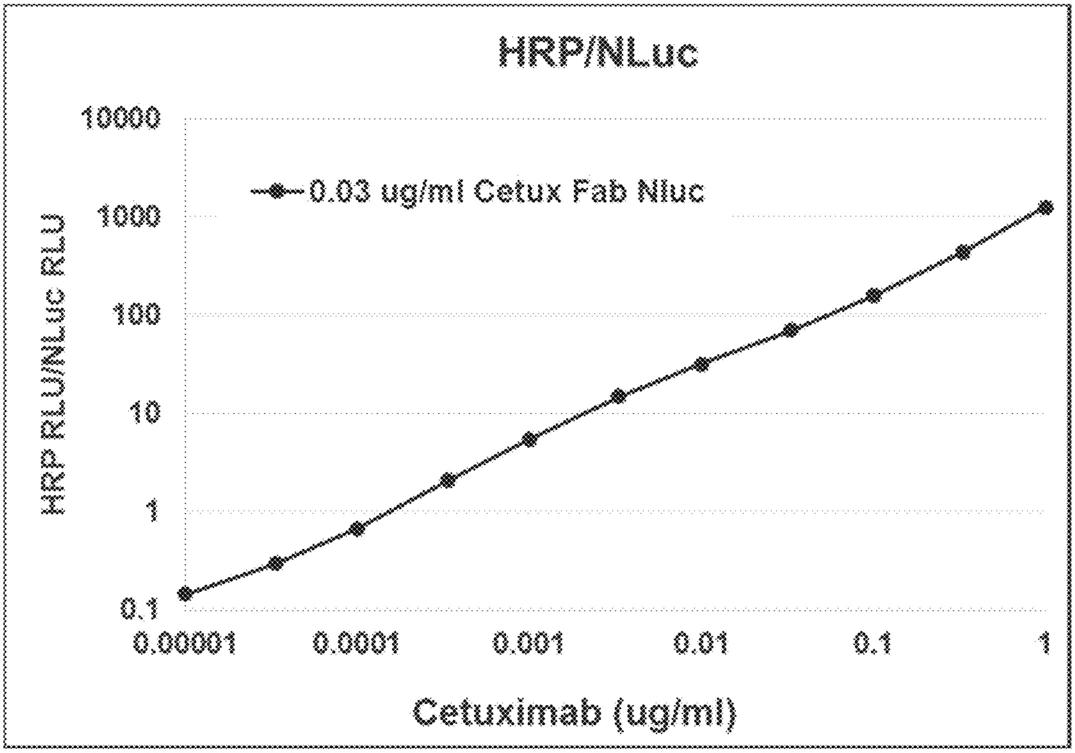
FIG. 2. Ratio of labeled detection reagent signal to labeled competitor signal as a function of Cetuximab concentration for two-reporter immunoassay.
Figure 3:
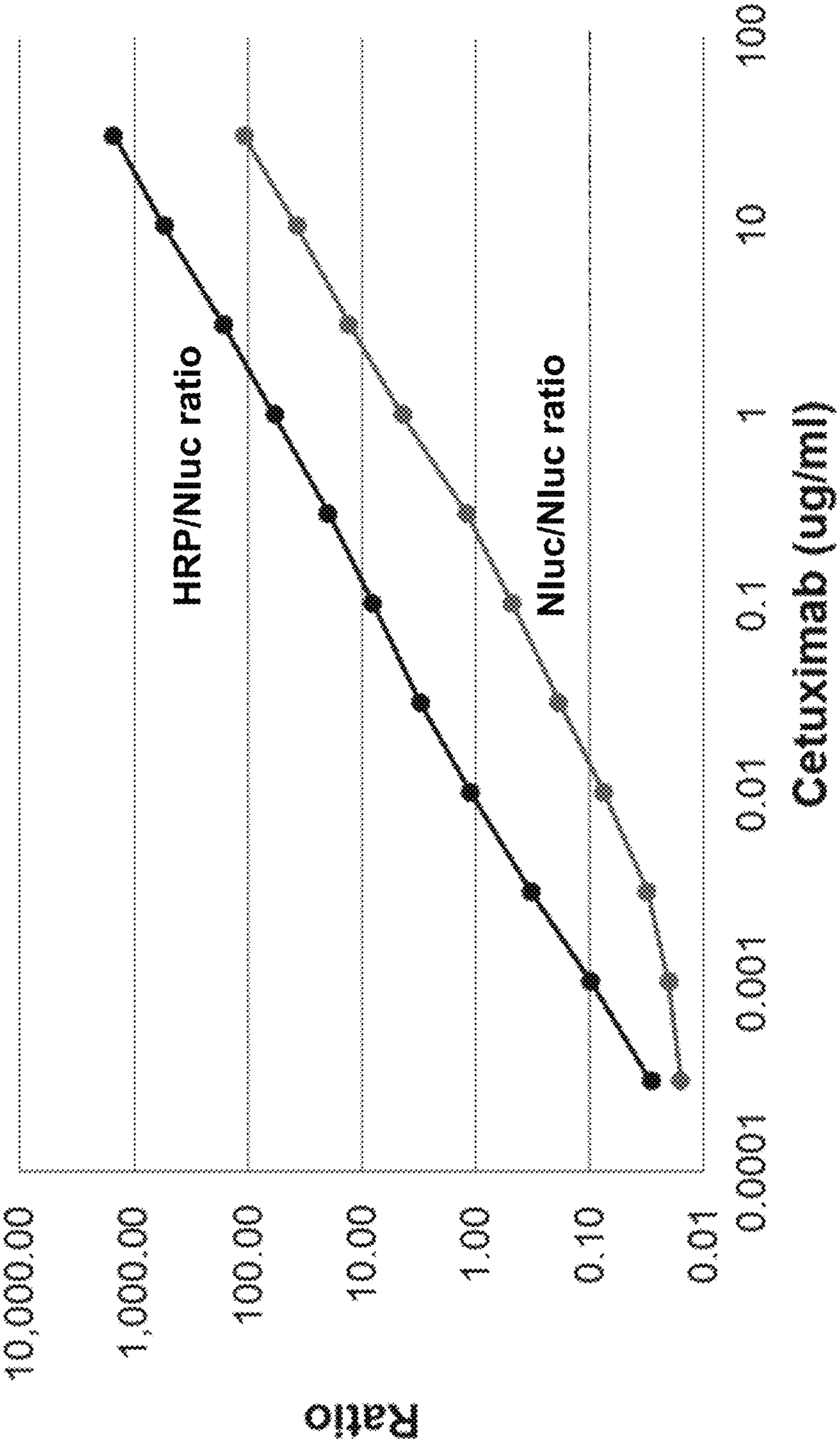
FIG. 3. Comparison of the ratios generated from immunoassays for single-reporter and two-reporter combined immunoassays.
Figure 4A:
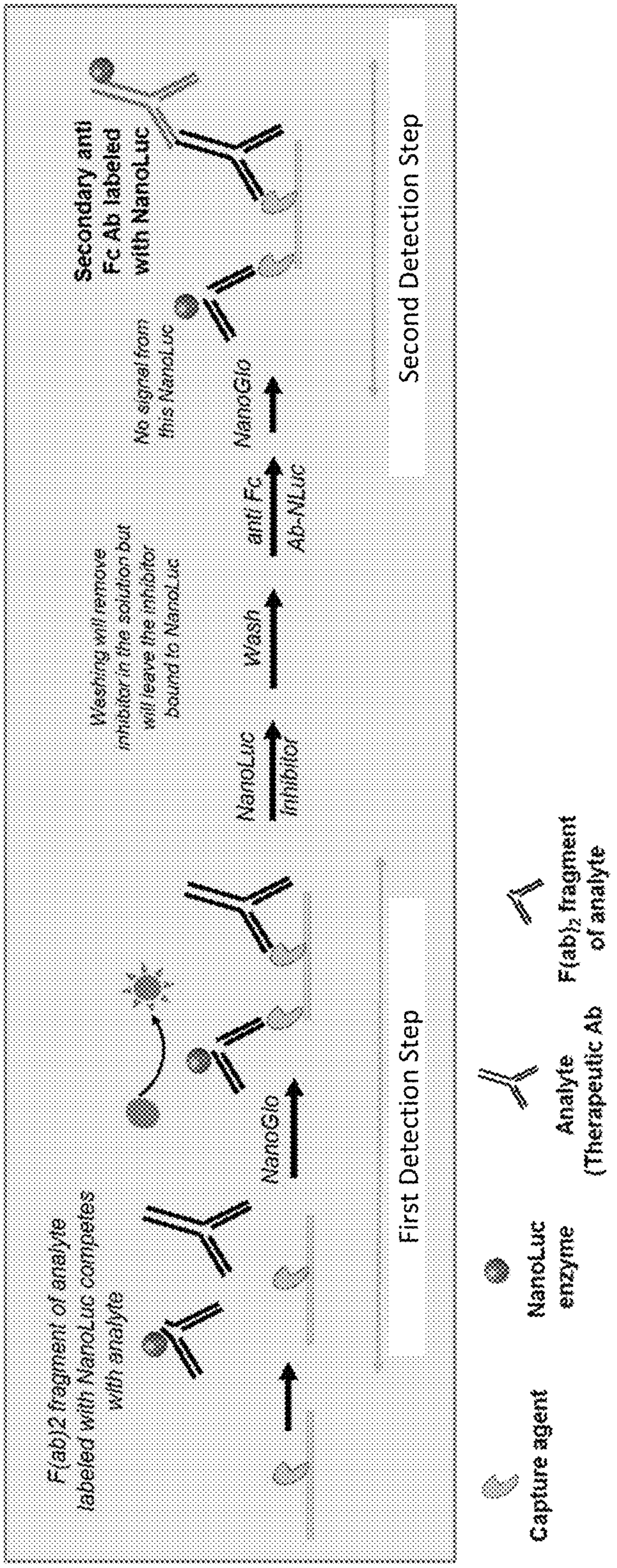
FIGS. 4A-B. Schematic representations of (FIG. 4A) two reporter and (FIG. 4B) one-reporter immunoassays.

1) A combined assay was designed and performed for detection of the anti-EGFR therapeutic antibody, Cetuximab, using a two-reporter system (FIG. 4A). For the labeled competitor, Cetuximab was cleaved into $F(ab)_2$ and Fc fragments using IdeS protease enzyme (Promega catalog #V7511). The Fc portion of the antibody was removed using magnetic Protein A beads (Promega), leaving behind the $F(ab)_2$ fragment of the Cetuximab. The Cetuximab $F(ab)_2$ was then labeled with NANOLUC® luciferase using chemical conjugation (the labeled competitor). Increasing amounts of a sample containing Cetuximab was added to a plate containing surface-immobilized EGFR, in the presence of a constant concentration of NANOLUC® luciferase-labeled Cetuximab $F(ab)_2$. FIG. 1A depicts the decrease in signal with increasing concentration of Cetuximab. The limit of detection (LOD) was approximately 0.01 ug/ml, and the upper limit of quantitation (ULOQ) was approximately 1.0 ug/ml in this assay. After the first detection step, the plate was washed then incubated with anti-human Fc secondary antibody labeled with HRP as a labeled detection agent (FIG. 1B). A dynamic range of 0.00001-0.01 was observed for second detection step of the assay. Using separate graphs for the two portions of the immunoassay (FIG. 1) allows detection of Cetuximab spanning at least 5 log orders of magnitude. A single dimensionless quantity is obtained by taking the ratio of the signal from the second detection (signal from the labeled detection agent) to the signal from the first detection (signal from the labeled competitor) (FIG. 2). This provides an intuitive and easily interpretable result in which the signal ratio increases with increasing concentration, clearly demonstrating the >5 log order dynamic range (FIG. 3). Additionally, using the ratio eliminates potential confusion that may be caused by widely different absolute signals.

Example 2

Single-Reporter Immunoassay

Figure 4B:
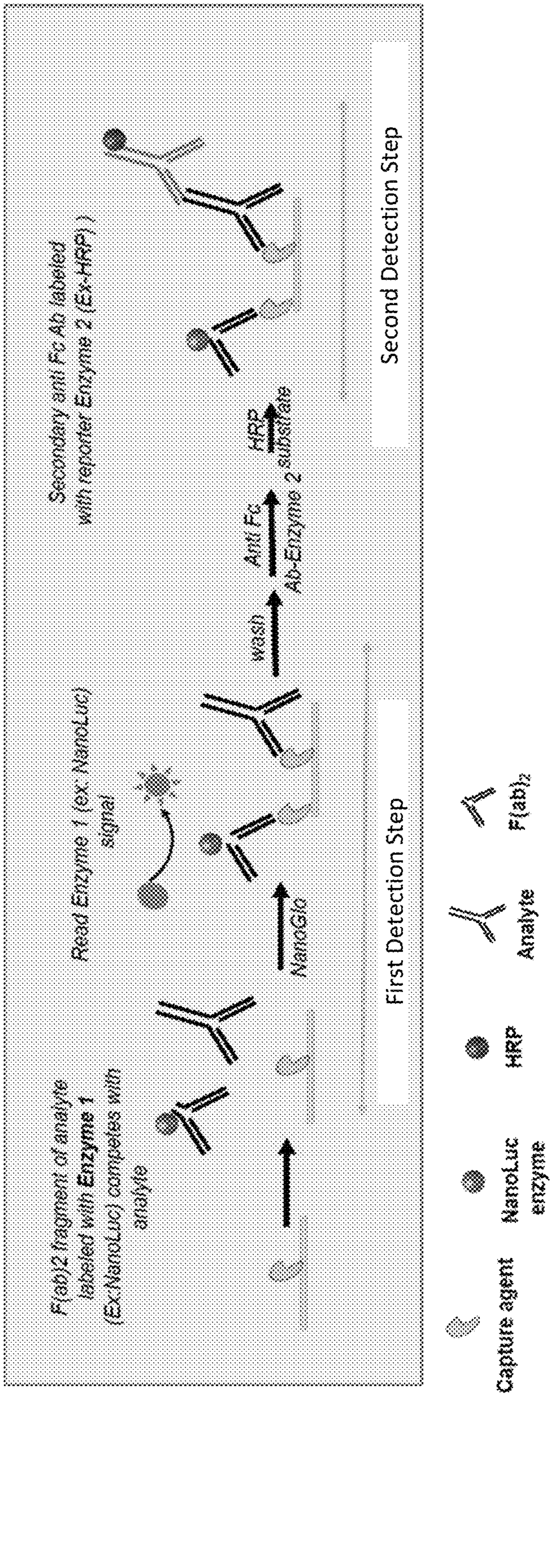

A combined assay was designed and performed for detection of the anti-EGFR therapeutic antibody, Cetuximab, using a single-reporter system (FIG. 4B). The IdeS-cleaved Cetuximab $F(ab)_2$ labeled with NANOLUC® luciferase was used as the labeled competitor. As above, a first detection step was performed by adding increasing amounts of Cetuximab to a plate containing surface-immobilized EGFR, in the presence of a constant concentration of NANOLUC® luciferase-labeled Cetuximab $F(ab)_2$. A NANOLUC® luciferase inhibitor, JRW-0552 was then used to eliminate signal from the NANOLUC® luciferase-labeled Cetuximab $F(ab)_2$. The plate was then washed and incubated with anti-human Fc secondary antibody labeled with NANOLUC® luciferase (labeled detection reagent). The ratio of signals from two detection steps of the assay (detection of labeled competitor and detection of labeled detection reagent) was plotted (FIG. 3) for Cetuximab along with that from the two-reporter system depicted in FIG. 2. Data from the experiments conducted during development of embodiments herein demonstrates the high dynamic range of the combined immunoassays.

JRW-0552

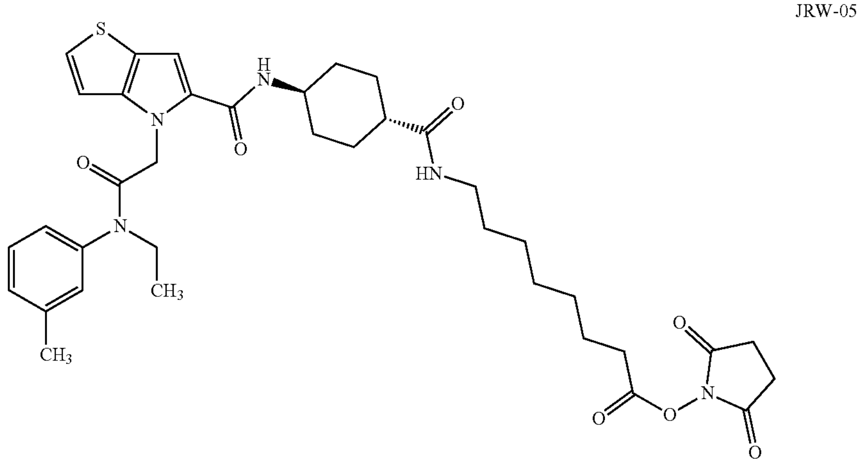

We claim:

1. A system comprising reagents for performing an immunoassay for the detection of a target analyte comprising:
   (a) a surface displaying capture agents that the target analyte is capable of stably binding;
   (b) a luciferase-labeled competitor capable of binding to the capture agents;
   (c) a luciferase-labeled detection agent comprising the same luciferase label as the luciferase-labeled competitor and capable of binding to the target analyte but not the competitor; and
   (d) an inhibitor of the luciferase label, wherein the inhibitor is capable of binding to the luciferase-labeled competitor and reducing the signal from the luciferase label.

2. The system of claim 1, further comprising a sample containing the target analyte.

3. The system of claim 1, wherein the system comprises a known amount of luciferase-labeled competitor and an unknown amount of target analyte.

4. The system of claim 1, wherein the surface is a slide, the interior of a tube, a plate, or the interior of a microwell.

5. The system of claim 1, wherein the target analyte is a target antibody.

6. The system of claim 5, wherein the target antibody is a therapeutic antibody.

7. The system of claim 5, wherein the capture agent comprises an epitope of the target antibody.

8. The system of claim 7, wherein the competitor comprises an $F(ab)_2$ fragment that is capable of binding the epitope of the target antibody.

9. The system of claim 8, wherein the detection agent comprises an anti-Fc antibody that is capable of binding the target antibody but not to the $F(ab)_2$ fragment.

10. The system of claim 1, wherein the inhibitor prevents substrate association with the luciferase.

11. The system of claim 1, wherein the inhibitor prevents substrate turnover by the luciferase.

* * * * *